United States Patent
Karadsheh

(10) Patent No.: US 10,898,390 B2
(45) Date of Patent: Jan. 26, 2021

(54) METHOD AND COMPRESSION GARMENT FOR ESTABLISHING A COMPRESSION TO A HUMAN LIMB OR BODY PART

(71) Applicant: SIGVARIS AG, St. Gallen (CH)

(72) Inventor: Daniel W. Karadsheh, Zeeland, MI (US)

(73) Assignee: Sigvaris AG, St. Gallen (CH)

( * ) Notice: Subject to any disclaimer, the term of this patent is extended or adjusted under 35 U.S.C. 154(b) by 596 days.

(21) Appl. No.: 15/443,308

(22) Filed: Feb. 27, 2017

(65) Prior Publication Data
US 2018/0243143 A1   Aug. 30, 2018

(51) Int. Cl.
  *A61F 13/02* (2006.01)
  *A61F 13/08* (2006.01)
  *A61F 13/06* (2006.01)

(52) U.S. Cl.
  CPC ........ *A61F 13/0273* (2013.01); *A61F 13/062* (2013.01); *A61F 13/08* (2013.01); *A61F 13/085* (2013.01)

(58) Field of Classification Search
  CPC ................ A61F 13/08; A61F 13/085; A61F 2013/0028; A61F 13/0273;
  (Continued)

(56) References Cited
  U.S. PATENT DOCUMENTS
  3,613,679 A   10/1971 Bijou
  5,904,145 A    5/1999 Reid
  (Continued)

FOREIGN PATENT DOCUMENTS
  CA    2 722 146 A1   10/2009
  WO    99/30607 A2    6/1999
  (Continued)

OTHER PUBLICATIONS

International Search Report for International Application No. PCT/EP2018/051917 dated Mar. 12, 2018.

*Primary Examiner* — Ophelia A Hawthorne
(74) *Attorney, Agent, or Firm* — McCormick, Paulding & Huber PLLC

(57) ABSTRACT

A method for establishing a compression level to a human limb or body part by a compression garment is shown, the garment consisting of or including a bandage having at least one closing part, which closing part is securable on the garment in a position wherein the bandage is fully or partly wrapped around said limb or body part to establish said pressure level, the method including
  a first step of wrapping the bandage around the limb or body part and provisionally securing it in a first position that holds the compression garment on the limb or body part without applying a compression level to said limb or body part;
  a second step of applying a tab with an adhesive or attaching mechanism to the garment, the tab abutting the terminal edge of the closing part;
  a third step of releasing the closing part from its provisionally secured position and wrapping the bandage part further around the limb or body part, using the length of the tab as a marking for a safe compression level range; and
  a fourth step of securing the closing part to the garment at a second position within the safe compression level range.

13 Claims, 5 Drawing Sheets

(58) Field of Classification Search
CPC .......... A61F 2013/00119; A61F 13/108; A61F 15/006; A61F 2013/00174; A61F 2013/00468; A61F 13/00008; A61F 13/022; A61F 13/0269; A61F 2013/00565; A61F 2013/00957; A61F 5/37; A61F 2013/00131; A61F 15/004; A61F 2013/00093; A61F 13/00029; A61F 13/00034; A61F 13/0226; A61F 13/066; A61F 13/533; A61F 13/55185; A61F 13/62; A61F 2007/0231; A61F 2013/00123; A61F 2013/00604; A61F 2013/00765; A61F 13/00004; A61F 2013/00089; A61F 2013/00102

See application file for complete search history.

(56) References Cited

U.S. PATENT DOCUMENTS

| | | | |
|---|---|---|---|
| 6,196,231 | B1 | 3/2001 | Reid |
| 6,338,723 | B1 | 1/2002 | Carpenter et al. |
| 6,516,804 | B1 | 2/2003 | Hoffman |
| 7,329,232 | B2 | 2/2008 | Lipshaw et al. |
| 9,364,701 | B2 | 6/2016 | Bartsch |
| 2006/0201032 | A1 | 9/2006 | Ramsey |
| 2010/0269240 | A1 | 10/2010 | Weir et al. |
| 2010/0312160 | A1 | 12/2010 | Creighton et al. |
| 2011/0125183 | A1 | 5/2011 | Lipshaw et al. |
| 2011/0185508 | A1 | 8/2011 | Hsu et al. |
| 2011/0257575 | A1* | 10/2011 | Farrow .................. A61F 13/08 602/75 |
| 2012/0179084 | A1* | 7/2012 | Lipshaw ............... A61F 13/085 602/75 |
| 2012/0277073 | A1 | 11/2012 | Bartsch |
| 2013/0283500 | A1 | 10/2013 | Lipshaw et al. |
| 2013/0319128 | A1 | 12/2013 | Richardson et al. |
| 2015/0025424 | A1 | 1/2015 | Richardson et al. |
| 2016/0030267 | A1 | 2/2016 | Lipshaw et al. |

FOREIGN PATENT DOCUMENTS

| | | |
|---|---|---|
| WO | 00/15139 A2 | 3/2000 |
| WO | 01/89410 A2 | 11/2001 |
| WO | 2013/085445 A1 | 6/2013 |
| WO | 2013/138394 A1 | 9/2013 |
| WO | 2015/188158 A2 | 12/2015 |
| WO | 2016/105213 A1 | 6/2016 |

* cited by examiner

METHOD AND COMPRESSION GARMENT FOR ESTABLISHING A COMPRESSION TO A HUMAN LIMB OR BODY PART

TECHNICAL FIELD

The invention relates to a method for establishing a compression level to a human limb or body part by a compression garment. The invention further relates to a compression garment for establishing a compression level to a human limb or body part.

BACKGROUND ART

Compression garments for providing compression to a limb or body part of a patient are well known. Such compression garments can be provided as bandages to be wrapped around the limb or body part, as a combination of a sleeve and a bandage part to be wrapped around or in other forms known to the skilled person. Such compression garments may include parts of stretchable (elastic) materials and/or parts of non-stretchable (inelastic) materials. When compression garments are used by a patient, the question may arise how much compression has to be applied. U.S. Pat. No. 6,338,723 suggests to use indicia on a stretchable, elastic part of the garment, which indicia are indicative on the amount of stretch of this part from a reference position, and a corresponding card with a scale for use with the indicia on the stretchable part is provided to set the stretch and a corresponding compression. This solution needs to provide indicia on the garment itself and can only be applied if a stretchable part is present. US-Patent Application Publication No. 2013/0283500 A1 suggests to apply a textile portion with a specific elastic profile to the basic textile having a different elastic profile in order to change the elastic profile of the garment. U.S. Pat. No. 9,364,701 describes a method of developing the accessory muscles of the upper torso of a patient using a therapy device having an adjustable compressive wrap. The device may have one or more markers attached to the wrap to indicate to the therapist where an attachment device should be attached to achieve the desired compression of the chest. U.S. Pat. No. 6,196,231 describes an apparatus for treating lymphedema. Marker elements are described to be placed on strap ends to indicate the degree of tightness that a release strap must be tightened to achieve a predetermined pressure measured by a pressure gauge.

SUMMARY

It is an object of the invention to provide the individual patient having to put on and wear a compression garment with an easy to apply method for establishing a safe level of compression and avoiding the selection of a level of compression that may be too high.

This object is met by a method for establishing a compression level to a human limb or body part by a compression garment, said garment consisting of or including a bandage having at least one closing part, which closing part is securable on the garment in a position wherein the bandage is fully or partly wrapped around said limb or body part to establish said pressure level, the method including a first step of wrapping the bandage around the limb or body part and provisionally securing it in a first position that holds the compression garment on the limb or body part without applying a compression level to said limb or body part;

a second step of applying a tab with an adhesive or attaching mechanism to the garment, the tab abutting the terminal edge of the closing part;

a third step of releasing the closing part from its provisionally secured position and wrapping the bandage further around the limb or body part, using the length of the tab or a marking on the tab as a marking for a safe compression level range; and the fourth step of securing the closing part to the garment at a second position within the safe compression level range as indicated by the tab.

This method can be applied with elastic and inelastic garments. In the most basic form, the garment may be a compression bandage. Compression garments using more parts and in particular having a sleeve for the limb and one or more bandage parts will work equally fine with the method according to the invention. The invention enables the patient to easily establish a safe maximum compression and thereby avoiding overpressure. After the patient has applied the garment to his/her limb or body part in a first position in which the garment just holds on to the limb or body part in the position for starting to apply compression, the tab belonging to the garment and having a certain, predetermined dimension, is placed and secured to the garment adjacent to the end of the closing part. By its dimension and in particular its length, or by a marking on the tab, the tab defines a distance for further wrapping of the garment around the limb or body part and therefore applying compression to the limb or body part. The tab belonging to the garment is dimensioned such that if the bandage of the garment is pulled by the user to apply compression, and therefore the bandage is further wrapped around the limb or body part and then secured by its closing part within the dimension of the tab a compression not exceeding a safe amount is established. Thus the user can be sure not to over-compress the limb or body part. The at least one closing part of the garment provided to securing the garment in the compression state may be of the hook and loop type, or known as VELCRO® fasteners, or may comprise of or include other known fastening means.

By a preferred embodiment of the method, wherein the tab length is indicative of the safe compression level and at the same time of a preferred compression level and in the fourth step the closing part is secured at a position so that its terminal edge aligns with the terminal edge of the tab, the tab not only assures that compression is within a safe level, but additionally indicates and provides for a preferred compression level that is safe and particularly useful.

By a further preferred embodiment of the method, the tab includes a marking on its surface which indicates a minimum preferred compression level and in the fourth step the closing part is secured with its terminal edge in a position wherein this terminal edge aligns with the marking, or in the fourth step the closing part is secured with its terminal edge in a position between the marking and the terminal end of the tab. Positioning the terminal edge of the closing part between the minimum marking on the tab and the end of the tab provides for a range of positions or compression levels, ranging from a minimum to a safe maximum compression level. Providing at least one additional marking in between such a minimum compression level marking and the end of the tab may further provide guiding marks for the user enabling the user to re-establish a preferred compression level when putting on the garment again.

It is preferred that the tab can be attached to the garment by a hook and loop type attaching mechanism, known as well as VELCRO® fastening means.

It is another object of the invention to provide a compression garment that allows for an easy and safe establishment of the level of compression and avoids the selection of a level of compression that may be too high.

This object is met by a compression garment for establishing a compression level to a human limb or body part, wherein the compression garment consists of or includes a bandage having a closing part that is securable on the garment in a position wherein the bandage is fully or partly wrapped around the human limb or body part to establish said pressure level, and wherein the compression garment includes a tab with an adhesive or with an attaching mechanism making the tab securable to the garment, the tab having a length that is adapted to the compression garment, so that the length of the tab is indicative of a safe compression level range when the bandage is wrapped around the limb or body part.

This garment can be an elastic or an inelastic garment. In the most basic form, the garment comprises of a bandage with a closing part only. Compression garments using more parts and in particular compression garments including a sleeve for the limb in addition to the bandage are encompassed by the invention as well. The garment according to the invention enables the patient to easily establish a safe compression level and to avoid overpressure. After the patient has applied the garment to his/her limb or body part in a first position in which the garment just holds on to the limb or body part in the position to start applying compression, the tab belonging to the garment and having a certain, predetermined dimension, is adapted to be placed and secured to the garment adjacent to the end of the closing part of the bandage that will be used by the patient to apply pressure to the limb or body part. By its dimension and particularly by its length, the tab defines a distance for further wrapping the bandage around the limb or body part and therefore applying compression to the limb or body part. The tab belonging to the garment is dimensioned such that if the bandage of the garment is pulled by the user to apply compression, and therefore the bandage is further wrapped around the limb or body part and then secured by the closing part to the garment within the dimension of the tab and thus overlaying the tab a compression not exceeding a safe amount is established. Thus the user of the garment according to the invention can be sure not to over-compress the limb or body part. The securing part of the garment may be of the hook and loop type, known as VELCRO® fasteners, or may comprise of other known fastening means.

In a preferred embodiment of the compression garment the tab is provided with at least one marking to provide a minimum compression marking. More markings may be present on the tab surface to provide pressure level indicators within the minimum compression level and the maximum safe compression level indicated by the terminal end of the tab.

In another embodiment of the compression garment, the garment includes at least two closing parts and a tab for each closing part. In such an embodiment with at least two closing parts, it is preferred that a section of each closing part and each tab are marked in order to indicate which tab belongs to which closing part. This marking can in particular be provided by corresponding colors on the closing part and the corresponding tab.

BRIEF DESCRIPTION OF DRAWINGS

The above and other features and advantages of the present invention will become more apparent to those of ordinary skill in the art by describing in detail preferred embodiments thereof with reference to the attached drawings in which.

DETAILED DESCRIPTION

Examples of the method and compression garments according to the invention are now described in more detail with reference to FIGS. 1 to 7. The compression garments are made from the usual materials used for manufacturing compression garments. Such materials are known to the skilled person. In particular, the materials are different kinds of textiles which can be said as being elastic textiles or inelastic textiles within the range of forces that occur during the use of compression garments. Accordingly, the compression garments may be made of elastic materials only or may be made of inelastic materials only, or such garments may be made from a combination of elastic and inelastic materials, in particular textiles. The textiles or other materials forming together the compression garments may be connected to each other by sewing, laminating, bonding, by adhesives or glues, or by other methods or means known to the skilled person. The compression garments may be provided in form of simple, rectangular bandages or may be provided with more functional parts and accordingly may include more complex shapes than a bandage.

Figure 1:
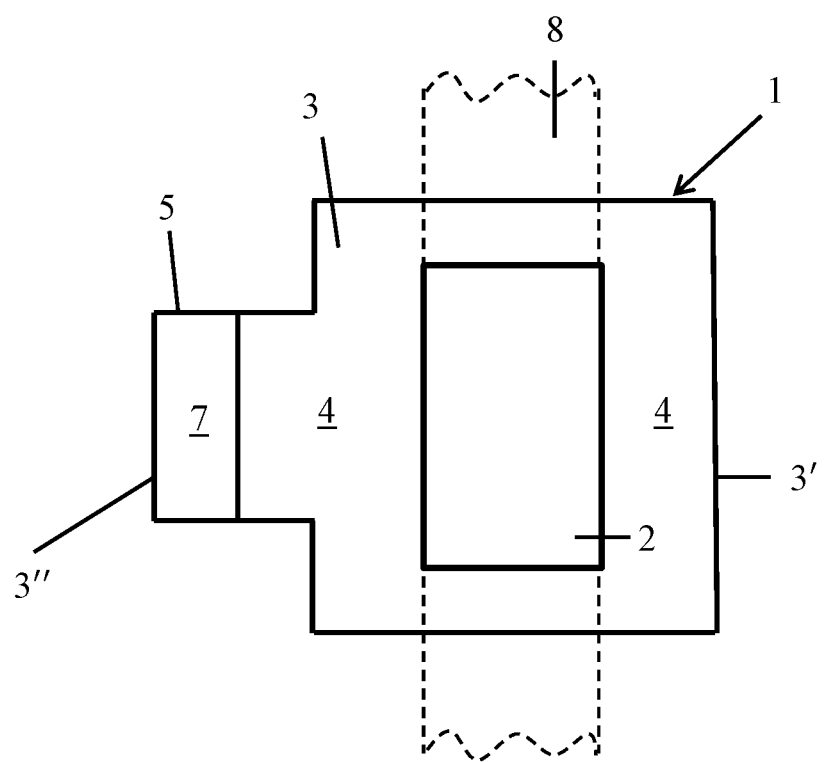
FIG. 1 shows a schematic view of a compression garment in an open, unwrapped state.

In FIG. 1 an example of a compression garment 1 is shown in a front view to the inside of the garment, the garment laying on a flat surface in opened, unfolded state. This example of the compression garment 1 includes a sleeve 2 within the inside 4 of the garment body 3. The mostly rectangular shaped garment body 3 can be said to be a bandage. If the sleeve 4 would not be present, the garment would thus be provided only by a bandage. The bandage includes in this example a closing part 5 which is reduced in height compared to the height of the rest of the body part 3 of the garment or bandage, respectively. The closing part may as well have the same height as the rest of the body part 3 or there may be more than one closing part. The closing part 5 serves for closing the garment in a manner known to the skilled person by securing it to the garment. It serves usually as well for grasping the compression garment by the user when wrapping the compression garment around the user's limb or body part. A terminal edge 3' of the garment body 3 is provided on one side of the garment body 3 and the other terminal edge 3" is provided at the other side of the garment body 3 provided by the closing part 5. The closing part may be a separate part of the garment body connected to the other parts of the garment body 3 or may be unitary with the other part of the garment body 3.

Of course, the compression garment and the closing part thereof may have other forms as shown. Functionally, the closing part is securable on the garment's outer side 6 in a position in which the garment is fully or partly wrapped around the human limb or body part to permanently establish a pressure level by the compression garment to the limb or body part during the time it is worn by the user. The closing part 5 includes closing elements on its inside, indicated here by reference numeral 7. Such closing elements may come in many forms known to the skilled person and serve to secure the closing part 5 to the outside 6 of the compression garment in order to close the garment after it has been wrapped around the limb or body part, and of course the closing elements are designed such that the garment can be opened again by the user. The outside 6 may include corresponding closing elements working together with the closing elements on the closing part 5. Such elements on the outside 6 will be provided at least in the area thereof where the closing part 5 comes to lie on the outside 6 when the compression garment is wrapped around the limb or body part of the patient. The closing elements may include hook and loop type fasteners, such as VELCRO® fasteners.

In the Figures, a part of a limb 8 is indicated by broken lines for indicating the position of the compression garment on a limb when it has been put on by a user of the garment. In case that the compression garment includes a sleeve 2, this sleeve will be pulled over the limb before the compression garment will be wrapped around the limb. This is indicated by the limb 8 position in FIG. 1.

Figure 2:
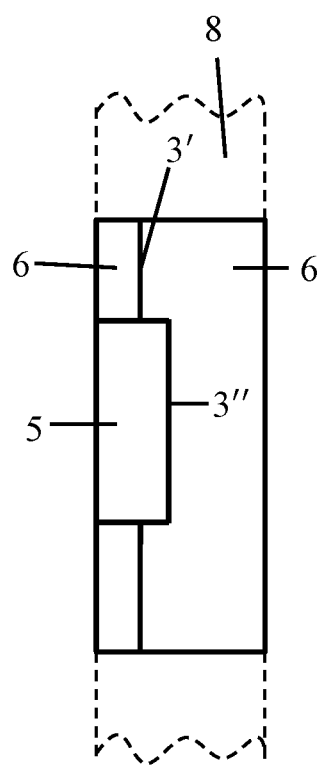
FIG. 2 shows the garment of FIG. 1 in a first state after a first step of wrapping the garment around a patient's limb.

FIG. 2 now shows the first step according to the method of the invention and shows that the compression garment has been wrapped around the limb 8 and has been provisionally secured in a first position that holds said compression garment on said limb or body part without applying a compression level to said limb or body part. By wrapping the compression garment around the limb, the outside 6 of the garment, which has not been visible in FIG. 1, is now visible. The provisional securing can be preferably done by the closing elements 7 working together with the outside of the garment. But under provisional securing within the meaning of the present invention it is also understood that this wrapping position, by which essentially no compression is applied yet, may be just held for a short while by hand by the user who has grasped the closing part 5 and has wrapped the garment around his/her limb or body part without applying a force that leads to a compression yet. But performing the following step is easier for the user when the provisional securing is done by using the closing part to secure the garment in the provisional position of the first step.

Figure 3:
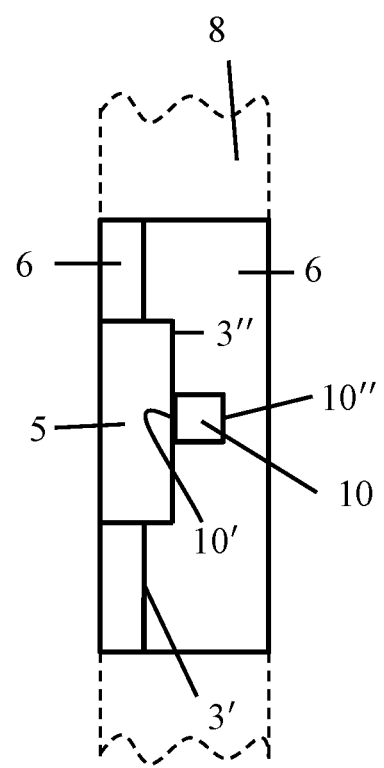
FIG. 3 shows the garment of FIG. 2 after a tab has been attached thereto in a second step.

FIG. 3 serves for explaining the next or second step of the invention in which a tab 10 with an adhesive or attaching mechanism is applied to the outside of the garment, the tab 10 abutting with its one edge 10' the terminal edge 3" of the closing part 5. The tab 10 may be a paper or plastic or textile tab or a tab from a combination of such materials or may be made from yet another material. It may be provided with an adhesive that holds the tab on the outside 6 of the garment body 3 when the tab is applied to the surface of the outside 6. The tab may as well include an attaching mechanism, as for example hook and loop fastener elements, which secures the tab to the outside 6 of the garment body 3. Thus, as shown in FIG. 3 the tab 10, which is a part of the garment and is adapted to the garment's properties, defines with its opposite edge 10" a safe margin for wrapping of the compression garment around the user's limb or body part. The tab may also include a marking near the edge 10", for example a line imprinted on the tab, that indicates the safe margin instead of the edge 10".

By the next step of the method, the garment will be wrapped further around the limb or body part of the user and will be definitively secured to apply the compression level that shall be established for the intended duration of use of the garment on the user's limb or body part. This is done by grasping the bandage by the user and in this case grasping the closing part 5 and wrapping it further around the limb 8 and securing the closing part 5 to the outside 6 of the garment body 3. The closing elements 7 of the closing part will attach to the outside of the garment to this end and in particular to corresponding closing elements provided on the outside 6. The tab 10 provides the user with a clear indication which is the safe margin of wrapping and thus compressing the limb 8 or body part, since the terminal edge 10" of the tab defines a limit indicator for wrapping and securing the closing part 5 around the limb. The length of the tab 10 of the compression garment is adapted to the properties of the compression garment providing the compression. If the compression garment is mainly comprised of inelastic material, the further amount of wrapping from the non-compressive starting position shown in FIG. 3 is smaller than for a compression garment which is mainly comprised of elastic material. Accordingly, the tab 10 is shorter in the first case since the safe wrapping distance translating to a safe compression level is usually shorter than for an elastic garment, which uses a longer wrapping distance for applying compression to the limb or body part. Instead of using the terminal edge 10" as the safe level of compression indicator, a marking on the tab may be used as mentioned before.

Figure 4:
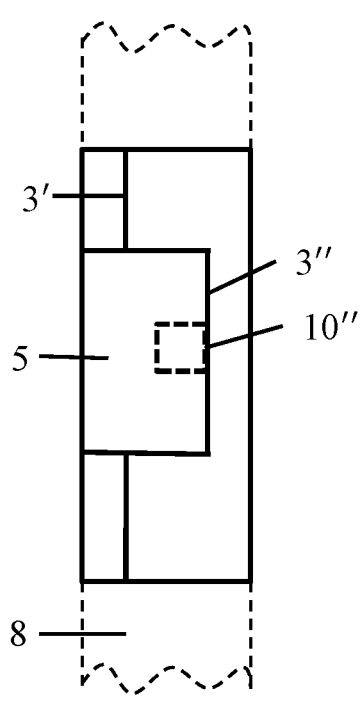
FIG. 4 shows the garment of FIGS. 2 and 3 after a third step of wrapping the garment further around the limb and after a fourth step of securing the garment, so that the garment is in its final position of wear by the user and wherein a pressure is established to the limb.
Figure 5:
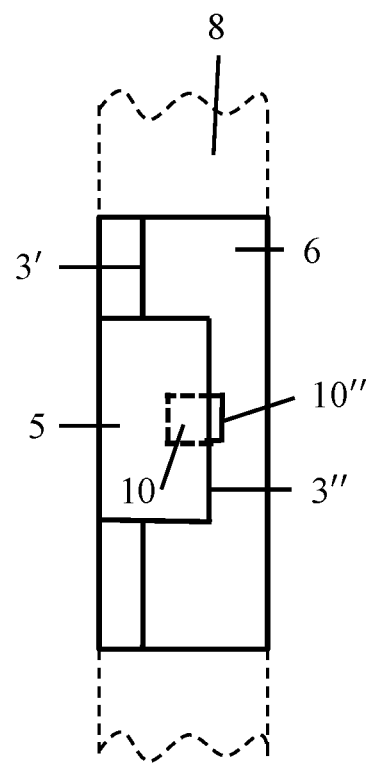
FIG. 5 shows an alternative position for securing the garment by the fourth step.

FIG. 4 shows the final position of the wrapped-around bandage or garment, respectively, wherein the terminal edge 3" of the closing part aligns with the terminal edge 10" of the tab 10. The tab 10 is covered in this position by the closing part 5 and is only indicated by dotted lines in FIG. 4. In this embodiment, the length of the tab indicates at the same time a preferred compression level and the maximum safe compression level. Instead of the terminal edge 10" a marking on the tab near this edge may be used as indicator as well. Further, it is possible for the user to select a final position of the closing part 5 which does establish a compression level lower than the maximum compression level indicated by the tab just by positioning the terminal edge 3" of the bandage or closing part 5, respectively, in a certain distance away from the terminal edge 10" of the tab which indicates the safe compression level (or from the marking on the tab indicating the safe compression level). Such a final position is shown in FIG. 5. The user can wear the garment in this position as well for the intended duration of use. It is preferred then, that the tab includes a minimum marking on the tab to help the user in selecting a useful minimum compression level, as will be later shown with reference to FIG. 7.

Figure 6:
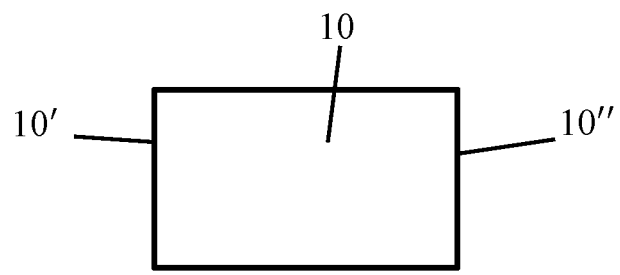
FIG. 6 shows a tab.

FIG. 6 shows a tab in its simplest form being provided by a rectangle made from one of the materials mentioned above. There are no markings on this tab 10 and its terminal edge 10' serves for placing the tab close to the edge 3" of the bandage during the second step of the method and the terminal edge 10" serves as the maximum compression level indicator, which may as well be the preferred level, as explained with reference to FIG. 4. Such tabs may come in paper form with an adhesive to be secured to the outside 6 of the garment. These tabs may be stored on a silicone paper and may be removed therefrom for a single use. When the garment is removed from the limb, the used tab will then be removed from the garment and discarded and for the next use of the garment a new tab will be pulled-off from the silicone paper. Such a tab 10 can as well be provided by a multi-use strip of a textile or by other embodiments of a tab.

Figure 7:
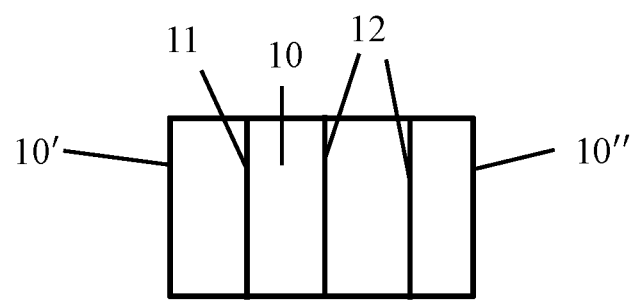
FIGS. 7 and 8 show other examples of a tab.
Figure 8:
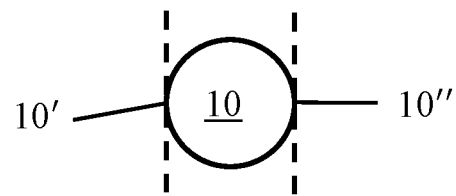

FIG. 7 shows another embodiment of a tab 10 having the terminal edges 10' and 10" which serve the purposes explained beforehand. This tab 10 can be a single or a multi-use tab as explained above as well. In addition to the indicator terminal edge 10" this tab 10 is provided with at least one marking 11 which is placed on the tab in order to indicate that a minimum useful compression level has been established, when the terminal end 3" of the garment is aligned with this marking 11. Additional markings 12 may be provided on the tab between the marking 11 and the terminal edge 10" indicator, in order to provide the user with markings to establish and in particular to re-establish a certain compression level preferred by the user when wearing the compression garment. Such markings can be made in different colors and may as well give indications of compression levels or ranges by numbers. FIG. 8 shows another embodiment of a tab 10. In this case the terminal edges 3' and 3" are mathematically given by a tangent on the circular tab, which tangents are of course not visible to the user but the user will be able to place and use such a tab with a sufficient exactness as well.

It may be that the garment includes more than one closing part. In this case there is at least one tab provided for one of the closing parts and the other closing part is then closed without the use of a tab by the user who establishes a compression level felt similar than the compression level established with the aid of the tab. It is preferred, however, when the second closing part is closed as well using the method and establishing a compression level by using a tab. The garment may be designed such that all closing parts can be used with a tab of the same dimension. The garment may be designed on the other hand such that tabs of different dimensions are to be used for different closing parts of the garment. In this case it is preferred to have the tabs and closing parts of the garment marked so that it is clear which tab shall be used for each closing part. The tabs and the closing parts may be color coded accordingly.

While there has been illustrated and described what is at present considered to be the preferred embodiment of the present invention, it will be understood by those skilled in the art that various changes and modifications may be made an equivalents may be substituted for elements thereof without departing from the true scope of the invention. Therefore, it is intended that this invention that this invention shall not be limited to the particular embodiments disclosed, but that the invention will include all embodiments falling within the scope of the appended claims.

What is claimed is:

1. A compression garment for establishing a compression level to a human limb or body part, wherein the compression garment consists of or includes a bandage having a closing part extending therefrom that is securable on the garment in a position wherein the bandage is fully or partly wrapped around the human limb or body part to establish said compression level, wherein the compression garment includes a tab with an adhesive or with an attaching mechanism making the tab securable to the garment, the tab having a length that is adapted to the compression garment, so that the length of the tab or a marking on the tab is indicative of a safe compression level range when the bandage is wrapped around the limb or body part.

2. The compression garment according to claim 1, wherein the tab is provided with a marking or with markings on its surface to provide at least one pressure level indication within said safe compression level range.

3. The compression garment according to claim 2, wherein the garment includes at least two closing parts and wherein a tab is included for each closing part.

4. The compression garment according to claim 1, wherein the garment includes at least two closing parts and wherein a tab is included for each closing part.

5. The compression garment according to claim 4, wherein a section of each closing part and each tab are correspondingly marked, and are in particular marked by corresponding colors, in order to define which tab belongs to which closing part.

6. The compression garment according to claim 1, wherein, when the bandage is fully or partly wrapped around the human limb or body part to establish said compression level, the closing part extends over at least a portion of the tab.

7. The compression garment according to claim 1, wherein the bandage is at least fully wrapped around said limb or body part.

8. A method for establishing a compression level to a human limb or body part by a compression garment, the garment consisting of or including a bandage having at least one closing part extending therefrom, which closing part is securable on the garment in a position wherein the bandage is fully or partly wrapped around said limb or body part to establish said compression level, the method including:
a first step of wrapping the bandage around the limb or body part and provisionally securing it in a first position with the at least one closing part so as to hold the compression garment on the limb or body part without applying a compression level to said limb or body part;
a second step of applying a tab with an adhesive or attaching mechanism to the garment, the tab abutting a terminal edge of the closing part;
a third step of releasing the closing part from the provisionally secured first position and wrapping the bandage further around the limb or body part, using a length of the tab or a marking on the tab as a marking for a safe compression level range; and
a fourth step of securing the closing part to the garment at a second position within the safe compression level range as indicated by the tab.

9. The method of claim 8, wherein the tab length is indicative of the safe compression level and at the same time of a preferred compression level and in the fourth step the closing part is secured at the second position so that the terminal edge of the closing part aligns with a terminal edge of the tab.

10. The method of claim 8, wherein the tab includes a marking on a surface which indicates a minimum preferred compression level and wherein in the fourth step the closing part is secured with the terminal edge of the closing part in a position wherein the terminal edge of the closing part aligns with the marking, or wherein in the fourth step the closing part is secured with the terminal edge of the closing part in a position between the marking and the terminal end of the tab.

11. The method of claim 8, wherein the tab is securable to the garment by a hook and loop type attaching mechanism.

12. The method according to claim 8, wherein the bandage is at least fully wrapped around said limb or body part.

13. The method according to claim 8, wherein, in the third step, the terminal end of the closing part is extended over at least a portion of the tab.

* * * * *